United States Patent [19]
Chen

[11] 4,082,950
[45] Apr. 4, 1978

[54] CALIBRATION ASSEMBLY FOR INFRARED MOISTURE ANALYZER

[75] Inventor: Leighton L. Chen, Greensboro, N.C.

[73] Assignee: Loew's Theatres, Inc., New York, N.Y.

[21] Appl. No.: 767,658

[22] Filed: Feb. 10, 1977

[51] Int. Cl.² ............................................. G01D 18/00
[52] U.S. Cl. .................................. 250/343; 250/252; 250/339; 356/243
[58] Field of Search ............... 250/252, 339, 343, 510; 356/243

[56] References Cited

U.S. PATENT DOCUMENTS

| | | | |
|---|---|---|---|
| 3,205,355 | 9/1965 | Ehlert | 250/339 X |
| 3,478,210 | 11/1969 | Janacek | 250/343 X |

*Primary Examiner*—Archie R. Borchelt
*Attorney, Agent, or Firm*—Brumbaugh, Graves, Donohue & Raymond

[57] ABSTRACT

A calibration assembly for an infrared moisture analyzer used for measuring the moisture content of tobacco leaf is described. The assembly comprises a housing for a glass window etched on at least one face and a layer of a particulate material having average particle sizes of about 50-100 microns. The assembly is characterized as having a reflectance similar to that of tobacco.

6 Claims, 3 Drawing Figures

CALIBRATION ASSEMBLY FOR INFRARED MOISTURE ANALYZER

BACKGROUND OF THE INVENTION

The determination of the moisture content of tobacco leaf is important to the tobacco processing industry. Frequently, the moisture content of tobacco leaf is measured with a reflectance type infrared analyzer. The instrument quantitatively measures the water content of solids by measuring the infrared reflectance of the sample to be analyzed in response to two infrared wavelengths, one within one of the water infrared absorption bands, and the second beam just outside of the water absorption band. The difference in the reflectance provides a measure of the moisture content of the sample. Water absorbs radiation in the near infrared region of the spectrum, which may be defined as the wavelengths extending between 0.8–2.5 microns. Characteristic absorptions for water are found at wavelengths of 1.9 and 1.4 microns. Accordingly, suitable reference wavelengths may be, for example, 1.6 and 1.2 microns.

In operation, the instrument must be empirically calibrated using samples of known moisture content. Typically, the instrument is provided with adjustments for the regulation of the "zero" point of the instrument and the "range" of moisture which will cause a full scale deflection. For calibration purposes, two or more samples of differing moisture contents generally covering the range of moisture content to be analyzed are tested. The zero point and range controls are adjusted so that meter readings for a normal moisture level will fall in a mid scale region. The range is adjusted so that the meter range will encompass the various moisture levels to be measured.

Because of drift in the characteristics of the instrument's meter circuitry, infrared moisture analyzers must be recalibrated periodically to vertify that the low and high meter readings have not changed in response to a pre-determined absorption levels. For this purpose, a double-sided black-white disc is usually supplied by the manufacturer. The disc is intended to provide a reproducible low reflectance and high reflectance calibration standard level which will be used for the purpose of recalibrating the instrument, if needed.

The commercially supplied discs, however, have been found to be unsatisfactory. In part, this is because the reflectivity of the discs in response to the infrared radiation employed in the instrument is not related to the reflectivity of the disc in response to visible light. Indeed, and surprisingly, it has been found that the reflectivity difference between the black and the white side of one commercial calibration disc in response to infrared radiation is negligible. Moreover, reflection from the disc is typically composed of both specular and diffuse reflection. In the commercial calibration disc, specular reflection is substantial. Specular reflection is critically dependent on the angular adjustment of the calibration disc relative to the optical path of the instrument. Where small differences in reflectivity must be calibrated, the use of the black-white disc results in readings which are not reproducible.

SUMMARY OF THE INVENTION

The present invention relates to a calibration assembly for an infrared moisture analyzer used for measuring the moisture content in solids. The novel assembly comprises a glass window etched on both faces and a layer of a particulate material having an average particle size of about 50–100 microns. The assembly has the advantage of being particularly useful for calibrating infrared moisture analyzers used for measuring the water content of tobacco leaf.

In accordance with the invention, a calibration assembly is provided which comprises (a) a housing, (b) a glass window which is transparent to infrared radiation, said window being etched on both faces and secured within the housing, (c) a layer of a particulate material contained within the housing beneath the window, said material having an average particle size in the range of about 50–100 microns, and (d) means to retain the particulate material layer within the housing. The assembly is characterized as having a reflectivity from the window with respect to the infrared wavelengths employed by the analyzer comparable to reflectivity of tobacco, and providing predominantly diffuse reflection from the window.

The housing may be constructed of any suitable material, such as metal, plastic or rubber, and may be of any shape for holding the glass window and particulate material, preferably ring-shaped. The housing may be equipped with means for mounting the assembly securely in an infrared moisture analyzer. Although any means will suffice, a housing having mounting grooves or devices corresponding to the mounting means of the analyzer will facilitate insertion and removal of the assembly.

As stated above, the window must be transparent to infrared radiation in the wavelength range used by the meter. In particular, the window should not absorb radiation in the near infrared region of the spectrum, the region in which water absorbs strongly. Glass which is composed primarily of silicon dioxide ($SiO_2$) is suitable for the window. Both faces of the glass window must be etched. The etching depth should be such as so to give a substantially covered rough surface whose roughness dimensions are substantially greater than the wavelength of the incident light (i.e., at least 10 microns). As a practical matter, etching will usually be much deeper. Typically, it is in the order of about 50 microns on the face of the glass window. For example, the glass window may be etched with No. 3 aluminum oxide powder. The glass window may be secured in the housing by any suitable means, for example, by epoxy cement.

The particulate material must have an average particle size in the range of about 50–100 microns, preferably about 50 microns. The particulate material contributes diffuse reflection which, in combination with the other contributing factors, assures that the total reflectance from the calibration assembly is similar to the total observed reflectance of tobacco leaf. The particulate material used for the assembly is closely packed to form a layer beneath the etched glass window. Sufficient packing is provided so that most of the infrared radiation entering the layer is either absorbed or reflected by it. The amount of incident radiation transmitted through the packing material should be negligible. To obtain this, the layer thickness may range from about one to three centimeters, preferably about 2 centimeters. The particulate layer may be secured within the housing by any suitable means. For example, a glass backing plate or a moisture impermeable substance placed behind the layer may be used. The backing is secured to the housing by an adhesive, such as epoxy cement.

For calibration, two assemblies are required to set the low and high readings on the meter. It has been found that two materials having the desired properties as described above are Florisil and Sephadex G-25 medium. Florisil, which is activated magnesium silicate gel, is used to set the high calibration reading. Sephadex, which is a chromatographic packing material made of cross-linked dextran gel, is used to set the low reading.

The assembly is designed to have a reflectance which simulates that of tobacco leaf. As used herein, tobacco leaf includes any of the known tobaccos, such as Turkish tobacco, burley tobacco, flue-cured tobacco and the like. Calibration assemblies described above may be adapted for use in any commercially available infrared reflectance anaylzer, for example the Anacon Model 106 Optical Moisture Analyzer used to determine the water content of a solid.

While the present invention is not limited in its dependence on any particular theory, an explanation for the selection of the materials for the calibration assembly described herein lies in an analysis of the major components of observed reflectance. A beam of incident infrared radiation may be absorbed, transmitted or reflected. Reflection can be of two types: diffuse or specular.

The absorption coefficient ($\alpha$) represents the fraction of incident energy which is absorbed by a given sample. The transmission coefficient (which is the fraction of incident energy transmitted) is significant only for materials which are transparent or translucent at the thickness employed. In the present case, the assembly contains a sufficient thickness of particulate material such that the transmitted radiation through the packing material is negligible. Hence in the present invention, the reflected radiation is the fraction $(1 - \alpha)$ of the incident radiation.

Diffuse reflection, resulting from surface roughness, is significant when the characteristic dimensions of the roughness of the sample surface are large relative to the wavelengths of the incoming radiation. Specular reflection, which may be attributed to smooth shiny surfaces, dominates when the dimensions of the surface roughness are materially less than the wavelength of the incident radiation.

For calibration instruments measuring the water content of tobacco leaves, it is desired that the calibration assembly have total reflectances (for the "high" and "low" calibration discs) at the wavelength employed in the instrument which are in the same range as exhibited by the tobacco leaf and which are reproducible.

In the present invention, reproducibility is assured by employing materials in the calibration disc assembly which provide a consistent diffuse reflection. When materials with predominant diffuse reflection terms are used, the observed reflection does not depend critically on the orientation of the assembly in the anaylzer. By comparison, the major contribution to the observed reflection of the black-white discs of the prior art is due to specular reflection. Specular reflection, resulting from surface smoothness, is greatly influenced by the orientation of the surface in the analyzer. Accordingly, imperceptible variations in the disc orientation in the analyzer can cause large differences in specular reflection which are uncontrolled and therefore cause calibration error.

The following approximations may be made for tobacco leaf. As indicated above, for a given measurement there will be two tobacco samples, one of known moisture content and the second sample whose moisture content is to be determined. Since tobacco is substantially opaque, substantially all of the incident radiation is either absorbed or reflected, that is, there is no significant transmission contribution. Moreover, since tobacco has a very rough surface, there is no material specular reflection, and differences in this factor between successive tobacco samples are negligible. Hence, as between successive samples of tobacco, the incident radiation is either absorbed or reflected, the degree of absorption varying with the tobacco sample. For successive tobacco samples differing only in moisture content, the observed reflectance difference is due solely to differing absorption at the water LC-absorption wavelength.

DESCRIPTION OF THE DRAWINGS

For a better understanding of this invention, reference may be made to the accompanying drawings.

Referring to FIG. 1, a ring-shaped housing 10 is manufactured into which the calibration assembly of the present invention is constructed. The ring-shaped housing 10 contains one or more mounting grooves 12 designed to fit the infrared moisture analyzer with which the calibration assembly is to be used. Centrally disposed within the housing 10 is a glass window 14 which is etched on both faces 16. Beneath the window is a layer of a particulate material which may be secured within the housing by any suitable means.

FIG. 2 shows the glass window 14, the particulate layer 18, and retaining means 20 in cross-sectional view. Both faces 16 of the glass window 14 are etched. Directly beneath the window there is provided a layer of a particulate material 18. The calibration assembly is completed by providing a suitable backing 20 to retain the particulate layer. Preferably, the backing is of a moisture impermeable substance, such as glass. To assure hermetic sealing, it is desirable to secure the window 14 and the backing 20 by a suitable adhesive such as epoxy cement or the like.

Figure 1:
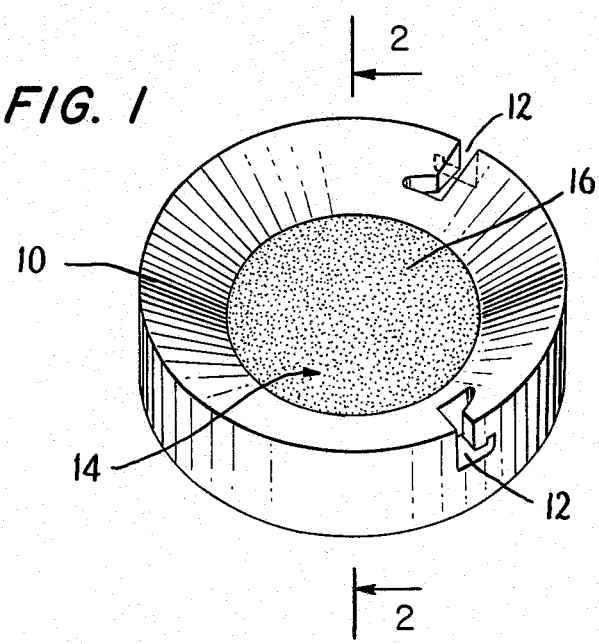
FIG. 1 is a drawing of a calibration assembly to accordance with the invention showing a ring-shaped housing, etched glass window, and mounting grooves for securing the assembly in an analyzer.
Figure 2:
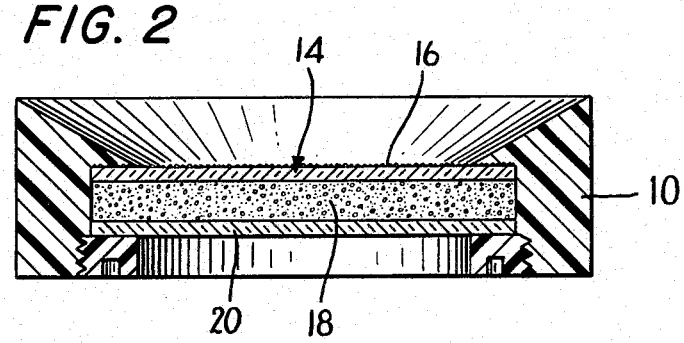
FIG. 2 is a cross-sectional view of the assembly of FIG. 1 showing the etched glass window, the layer of particulate material, and means for retaining the particulate material in the housing.
Figure 3:
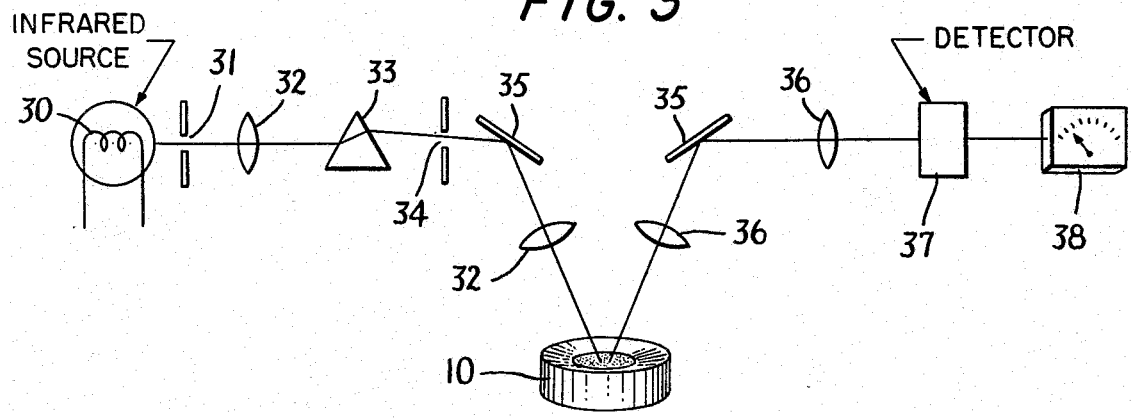
FIG. 3 is a schematic diagram of an infrared moisture analyzer showing the major components and the calibration assembly of the present invention.

A diagram of a typical infrared moisture analyzer for use in the present invention is illustrated in FIG. 3. It comprises an infrared radiation source 30, such as an incandescent light source, an entrance slit 31, one or more lenses 32 to focus an image onto the focal plane of the instrument, a prism 33, and an exit slit 34. The prism 33 is adjustably mounted so as to permit selection of the desired wavelength of light which is to be used for analysis. It will, of course, be obvious that diffraction gratings are commonly substituted for prisms in instruments of this kind. Mirrors 35 are typically provided to permit bending of the optical path so that it may be focused upon a suitable point somewhat external of the instrument housing where sample material to be analyzed will pass. The reflected light from the focal plane of the instrument is received by lenses 36 and focused onto an infrared detector 37. The infrared detector through appropriate circuitry is connected to a meter 38 which responds to the amount of moisture in the sample. The electronic circuitry may include a normal circuit for analysis, and the same or a separate circuit to facilitate calibration. A calibration assembly as illustrated in FIGS. 1 and 2 is shown at the focal plane of the instrument.

EXAMPLE

In accordance with the present invention, two calibration assemblies of the foregoing description are prepared, the two assemblies having somewhat different reflectance characteristics. One assembly forms a calibration standard for the zero setting or low calibration point of the instrument, and the second forms a calibration standard for the range or high calibration setting of the instrument. As noted above, activated magnesium silicate and cross-linked dextran gels have been found to be suitable particulate materials for the purposes of the present invention.

While the zero point may be set, if desired, to correspond to a sample of 0% moisture and the range adjusted to correspond to sample moisture variation between 0 and 100% moisture, for many purposes this is not done. With particular reference to the tobacco industry, tobacco samples encountered in commerce may typically have moisture contents ranging from 8–10% moisture up to possible 20–25% moisture. It is desired to control the tobacco moisture to an intermediate value, for example 15%.

For the analysis of tobacco of this type, it is convenient and more accurate to adjust the "zero" point of the instrument to correspond to a tobacco of 10% moisture and the range of the instrument is set to provide meaningful readings for tobacco having moisture contents varying up to 20% moisture.

Initially, the instrument is calibrated by preparing tobacco samples of known moisture contents, as determined by conventional quantitative analysis (e.g. moisture loss on over drying), one sample having a moisture content of 10% and a second sample having a moisture content of, for example, 20% with the instrument set for normal analysis. The tobacco samples of known moisture content are employed to adjust the zero point and range of the instrument so that the lowest meaningful readings on the instrument will correspond to 10% moisture and the highest meaningful instrument reading will correspond to 20% moisture. Immediately upon the initial calibration of the instrument in this manner and prior to any further use thereof, the two calibration assemblies of the invention are then placed in the focal plane of the instrument. The scale readings for the two calibration assemblies are then noted.

Thereafter, the instrument is employed for routine measurement of tobacco moisture content for laboratory or manufacturing control purposes. From time to time, when it appears that the instrument settings may have drifted and recalibration is required, the two calibration assemblies are successively placed in the focal plane of the instrument, and the zero point and scale adjustments are readjusted so that the instrument readings correspond to the two readings observed for the calibration assemblies at the time the instrument had been freshly calibrated with tobacco of known moisture content. After readjustment of the zero point and scale settings, the instrument is again returned to its measurement mode and placed back into service.

I claim:

1. A calibration assembly for an infrared moisture analyzer for measuring the moisture content of tobacco leaf by reflection of infrared radiation which comprises:
   (a) a housing having means for mounting in the moisture analyzer;
   (b) a glass window which is transparent to infrared radiation, said window being etched on both faces and secured within the housing;
   (c) a layer of a particulate material contained within the housing beneath the window, said material having an average particle size in the range of about 50–100 microns;
   (d) means to retain the particulate material layer within the housing; and
   (e) said assembly having a reflectivity from the window thereof with respect to the infrared wavelengths employed in said analyzer comparable to the reflectivity of tobacco, and providing a predominantly diffuse reflection from the window.

2. The assembly of claim 1 wherein the etched glass window is characterized by a surface roughness having dimensions substantially greater than the wavelength of the incident infrared radiation.

3. The assembly of claim 1 wherein the particulate material has an average particle size of about 50 microns.

4. The assembly of claim 1 wherein the particulate material is activated magnesium silicate gel.

5. The assembly of claim 1 wherein the particulate material is cross-linked dextran gel.

6. The assembly of claim 1 wherein the particulate material layer ranges in thickness from about 1–3 centimeters.

* * * * *